United States Patent
Sinha et al.

(10) Patent No.: US 7,582,452 B2
(45) Date of Patent: Sep. 1, 2009

(54) ASSAY FOR SPECIES SOURCES

(75) Inventors: Sudhir K. Sinha, Metairie, LA (US); Jaiprakash G. Shewale, Metairie, LA (US); Jerilyn A. Walker, Breaux Bridge, LA (US); Mark A. Batzer, Mandeville, LA (US)

(73) Assignees: Life Genetics Lab, LLC, New Orleans, LA (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 637 days.

(21) Appl. No.: 10/736,912

(22) Filed: Dec. 17, 2003

(65) Prior Publication Data

US 2005/0112592 A1     May 26, 2005

Related U.S. Application Data

(60) Provisional application No. 60/524,037, filed on Nov. 24, 2003.

(51) Int. Cl.
   *C12Q 1/68*       (2006.01)
   *C12P 19/34*    (2006.01)
(52) U.S. Cl. .......................... 435/91.2; 435/6; 435/91.1
(58) Field of Classification Search ................... None
   See application file for complete search history.

(56) References Cited

U.S. PATENT DOCUMENTS 6,174,670 B1 * 1/2001 Wittwer et al. ................. 435/6

2004/0146912 A1 * 7/2004 Lipton et al. .................. 435/6

OTHER PUBLICATIONS

Walker et al (Anal. Biochem. (May 2003) 316:259-269).*
Tajima et al (Biosci. Biotechnol. Biochem. (Oct. 2002) 66(10):2247-2250).*
Verkaar et al (Meat Science (2002) 60:365-369).*
Genbank Accession No. V00116 (1983).*
Buck et al (Biotechniques (1999) 27(3):528-536).*

* cited by examiner

*Primary Examiner*—Young J Kim
(74) *Attorney, Agent, or Firm*—Robert E. Bushnell, Esq.

(57) ABSTRACT

A family of PCR assays is disclosed for determining, both qualitatively and quantitatively, presence of material from a predetermined species source and for quantifying the amount of such material. The assays are based respectively on SINEs uniquely characteristic of pig species, cow species, chicken species, and ruminant sub-order, and having a high copy number. The assays disclosed permit rapid, inexpensive evaluation of meat samples to facilitate elimination from their diet of pork or beef by persons desiring to avoid such food sources; as well as the assay of cattle feed to determine presence therein of ruminant-source proteins, which are a potential source of bovine spongiform encephalopathy (BSE), commonly referred to as "mad cow disease." The assays amplify the predetermined unique SINEs and the resulting amplified mixture is then evaluated qualitatively by electrophoresis on gel containing ethidium bromide or quantitatively by SYBR Green-based detection or TaqMan chemistry. The invention also extends to kits, primers, and other products used in connection with the assays. The amplicons are selected to be from about 100 to 170 bp long.

6 Claims, 6 Drawing Sheets

ASSAY FOR SPECIES SOURCES

CLAIM OF PRIORITY

This application makes reference to, incorporates the same herein, and claims all benefits accruing under 35 U.S.C. §119 and §120 from a provisional application for ASSAY FOR SPECIES SOURCES earlier filed in the U.S. Patent & Trademark Office on 24 Nov. 2003 and there duly assigned Ser. No. 60/524,037.

BACKGROUND OF THE INVENTION

1. Technical Field

The present invention concerns assays for determining presence, and for quantitation, of species sources of DNA. More specifically, the invention concerns assay methods for detecting and quantitating ruminant-source material in animal feed and pork material in foods. In addition, the invention extends to assay methods for detecting and quantitating beef and chicken material in foods of mixed or complex sources, and to products used in performing the foregoing methods. In addition, the invention extends to detecting and quantitating ruminant-source, pork-source, beef-source, and chicken-source material in cosmetics and other substances, which may be ingested by humans.

2. Related Art

Animal Species Involved

With the exception of the chicken assay disclosed hereinafter, all of the assays described herein are directed to hoofed mammals of the order Artiodactyla. Within that order, two suborders are of interest here: Suiforms and Ruminantia. Within Suiforms the family Suidae is of interest because it includes the common pig, *Sus scrofa*. The Ruminantia ("cud-chewing" animals) as a whole are of interest, because of governmental disease-control guidelines and regulations discussed hereinafter. Within Ruminantia, the family of principal interest is Bovidae, which includes cattle (cows), sheep, and goats. Within Bovidae the principal species of interest is *Bos taurus*, whose meat (beef) is widely consumed; the species *Ovis aries* is also of some interest because its meat (lamb) is also widely consumed. Deer (*Odocoileus virginianus*, in Cervidae family) and antelope (*Antilocarpa americana* in Bovidae family) are also among the Ruminantia whose meat is consumed to some extent. The assays specifically described hereinafter involve animals used as food.

Mad Cow Disease

Bovine spongiform encephalopathy (BSE), commonly referred to as "mad cow disease," has a human form termed vCJD that is a variant of Creutzfeldt-Jakob disease, a fatal neurodegenerative disease that has caused many deaths in the United Kingdom. See P. Brown, Bovine spongiform encephalopathy and variant Creutzfeldt-Jakob disease, Br. Med. J. 322 (2001) 841-844. In response to the BSE epidemic in Europe, the United States Food and Drug Administration (FDA) imposed strict guidelines in 1997, prohibiting the use of ruminant-derived protein in the manufacture of animal feed intended for cows or other ruminants. It is widely believed that the practice of utilizing ruminant carcasses in animal feed for livestock is responsible for the spread of BSE to epidemic proportions. See P. Brown (2001), supra. As a result, the need for sensitive detection of ruminant species remains in animal feed is a paramount agricultural issue.

Pork and Beef Avoidance

The risk associated with infectious transmissible spongiform encephalopathy in humans has discouraged many individuals around the globe from consuming beef. Hindu populations also choose not to eat beef, while Jewish and Muslim populations choose to avoid consumption of pork, even in minute quantities, due to their religious beliefs. Many consumers prefer to include more chicken in their diet instead of beef or pork. In addition to concerns about infectious disease and religious concerns, many individuals are altering their eating behavior to include more chicken simply to reduce dietary fat intake in accordance with health trends. Other consumers, however, may avoid chicken because of fear of Salmonella infection. Any conceivable ambiguity in the labeling practices of commercial suppliers or grocery stores is unacceptable to these consumer subsets. The need for sensitive detection and quantitation of bovine, porcine, and chicken species in food and mixed-food products is critical in response to this consumer demand.

Prior Detection Methods

The quantitative detection of meat species sources in mixed food samples has been approached using a variety of different systems. Early approaches to identify species-specific components within mixed samples involved the use of high-performance liquid chromatography. See E. O. Espinoza, M. A. Kirms, M. S. Filipek, Identification and quantitation of source from hemoglobin of blood and blood mixtures by high performance liquid chromatography, J. Forensic Sci. 41 (1996) 804-811; H. I. Inoue, H. F. Takabe, O. Takenaka, M. Iwasa, Y. Maeno, Species identification of blood and blood-stains by high-performance liquid chromatography, Int. J. Legal Med. 104 (1990) 9-12. These methods have proven useful for the identification of many different animal species, but the detection limits using these approaches are restrictive. The detection of nuclear DNA sequences has also been useful in this regard, but is limited as a result of their generally low copy number. See R. Meyer, U. Candrian, J. Luthy, Detection of pork in heated meat products by the polymerase chain reaction, J. AOAC Int. 77 (1994) 617-622. Meat species identification using enzyme-linked immunosorbent assays, see F. C. Chen, Y. H. Hsieh, Detection of pork in heat-processed meat products by monoclonal antibody-based ELISA, J. AOAC Int. 83 (2000) 79-85, and protein profiles, see H. J. Skarpeid, K. Kvaal, K. I. Hildrum, Identification of animal species in ground meat mixtures by multivariate analysis of isoelectric focusing protein profiles, Electrophoresis 19 (1998) 3103-3109, have also been used.

But assays based on the polymerase chain reaction (PCR) are currently the method of choice for species identification. See J. H. Calvo, P. Zaragoza, R. Osta, A quick and more sensitive method to identify pork in processed and unprocessed food by PCR amplification of a new specific DNA fragment, J. Anim. Sci. 79 (2001) 2108-2112. PCR analysis of species-specific mitochondrial DNA sequences is the most common method currently used for identification of meat species in food, see B. L. Herman, Determination of the animal origin of raw food by species-specific PCR, J. Dairy Res. 68 (2001) 429-436; T. Matsunaga, K. Chikuni, R. Ranabe, S. Muroya, K. Shibata, J. Yamada, Y. Shinmura, A quick and simple method for the identification of meat species and meat products by PCR assay, Meat Sci. 51 (1999) 143-148; R. Meyer, C. Hofelein, J. Luthy, U. Candrian, Polymerase chain reaction-restriction fragment length polymorphism analysis: A simple method for species identification in food, J. AOAC Int. 78 (1995) 1542-1551; S. Lahiff, M. Glennon, L. O'Brien, J. Lyng, T. Smith, M. Maher, N. Shilton, Species-specific PCR for the identification of bovine, porcine and chicken species in meat and bone meal (MBM), Mol. Cell. Probes 15 (2001) 27-35; L. Partis, D. Croan, Z. Guo, R. Clark, T. Coldham, J. Murby, Evaluation of a DNA fingerprinting method for determining the species origin of meats, Meat Sci. 54 (2000) 369-376; J. F. Montiel-Sosa, E. Ruiz-Pesini, J. Montoya, P. Roncales, M. J. Lopez-Perez, A. Perez-Martos, Direct and highly species-specific detection of pork meat and fat in meat products by PCR amplification and mitochondrial DNA, J. Agric. Food Chem. 48 (2000) 2829-2832, and animal feedstuffs, see F. Bellagamba, V. M. Moretti, S. Comincini, F. Valfre, Identification of species in animal feedstuffs by polymerase chain reaction-restriction fragment length polymorphism analysis of mitochondrial DNA, J. Agric. Food Chem. 49 (2001); 3775-3781; M. Tartaglia, E. Saulle, S. Pestalozza, L. Morelli, G. Antonucci, P. A. Battaglia, Detection of bovine mitochondrial DNA in ruminant feeds: a molecular approach to test for the presence of bovine-derived materials, J. Food Prot. 61 (1998) 513-518; P. Krcmar, E. Rencova, Identification of bovine-specific DNA in feedstuffs, J. Food Prot. 64 (2001) 117-119.

The advantage of mitochondrial-based DNA analyses derives from the fact that there are many mitochondria per cell and many mitochondrial DNA molecules within each mitochondrion, making mitochondrial DNA a naturally amplified source of genetic variation. Recently, PCR-based methods have been reported that use multi-copy nuclear DNA sequences such as satellite DNA, see Z. Guoli, Z. Mingguang, Z. Zhijiang, O. Hongsheng, L. Qiang, Establishment and application of a polymerase chain reaction for the identification of beef, Meat Sci. 51 (1999) 233-236; J. H. Calvo, C. Rodellar, P. Zaragoza, R. Osta, Beef- and bovine-derived material identification in processed and unprocessed food and feed by PCR amplification, J. Agric. Food Chem. 50 (2002) 5262-5264, and repetitive elements, see J. H. Calvo, P. Zaragoza, R. Osta, A quick and more sensitive method to identify pork in processed and unprocessed food by PCR amplification of a new specific DNA fragment, J. Anim. Sci. 79 (2001) 2108-2112; K. Tajima, O. Enishi, M. Amari, M. Mitsumori, H. Kajikawa, M. Kurihara, S. Yanai, H. Matsui, H. Yasue, T. Mitsuhashi, T. Kawashima, M. Matsumoto, PCR detection of DNAs of animal origin in feed by primers based on sequences of short and long interspersed repetitive elements, Biosci. Biotechnol. Biochem. 66 (2002) 2247-2250. Like mitochondrial-based systems, these nuclear PCR-based assays take advantage of multiple target amplification sites in the genome of interest. However, many of these systems require additional procedural steps (such as endonuclease digestion) and at least 1-250 pg of starting DNA template for species detection. See J. H. Calvo, P. Zaragoza, R. Osta, A quick and more sensitive method to identify pork in processed and unprocessed food by PCR amplification of a new specific DNA fragment, J. Anim. Sci. 79 (2001) 2108-2112; J. H. Calvo, C. Rodellar, P. Zaragoza, R. Osta, Beef- and bovine-derived material identification in processed and unprocessed food and feed by PCR amplification, J. Agric. Food Chem. 50 (2002) 5262-5264. Also, Tajima and co-workers, see K. Tajima, O. Enishi, M. Amari, M. Mitsumori, H. Kajikawa, M. Kurihara, S. Yanai, H. Matsui, H. Yasue, T. Mitsuhashi, T. Kawashima, M. Matsumoto, PCR detection of DNAs of animal origin in feed by primers based on sequences of short and long interspersed repetitive elements, Biosci. Biotechnol. Biochem. 66 (2002) 2247-2250, recently reported the development of PCR assays for the detection of ruminant-, pig-, and chicken-derived materials based on sequences of short and long interspersed repetitive elements.

These assays exceed the detection limits of previously reported assays. See T. Matsunaga, K. Chikuni, R. Ranabe, S. Muroya, K. Shibata, J. Yamada, Y. Shinmura, A quick and simple method for the identification of meat species and meat products by PCR assay, Meat Sci. 51 (1999) 143-148; S. Lahiff, M. Glennon, L. O'Brien, J. Lyng, T. Smith, M. Maher, N. Shilton, Species-specific PCR for the identification of bovine, porcine and chicken species in meat and bone meal (MBM), Mol. Cell. Probes 15 (2001) 27-35; M. Tartaglia, E. Saulle, S. Pestalozza, L. Morelli, G. Antonucci, P. A. Battaglia, Detection of bovine mitochondrial DNA in ruminant feeds: a molecular approach to test for the presence of bovine-derived materials, J. Food Prot. 61 (1998) 513-518. However, there are several limitations to their methods. Primarily, the detection of PCR products is exclusively gel based and thus non-quantitative. In addition, the relatively large size of the PCR amplicons for the assays (179-201 bp) reported by Tajima and co-workers, see K. Tajima, O. Enishi, M. Amari, M. Mitsumori, H. Kajikawa, M. Kurihara, S. Yanai, H. Matsui, H. Yasue, T. Mitsuhashi, T. Kawashima, M. Matsumoto, PCR detection of DNAs of animal origin in feed by primers based on sequences of short and long interspersed repetitive elements, Biosci. Biotechnol. Biochem. 66 (2002) 2247-2250, may limit their utility for testing trace materials that contain degraded DNA (or truncated sequences).

Cosmetics and Other Materials

Inedible remnants of cows, sheep, and other animals are rendered into fat (or "tallow") as well as meat-and-bone meal. The fat "is used in an amazing array of products (such as soap, lipstick, linoleum, and glue)."Some of these products, such as lipstick and glue, may be ingested by human users. Considerations similar to those applying to meat may therefore apply to potentially ingested products such as lipstick that may contain ruminant-source, pork-source, or beef-source fat. Such products are thus a potential vector for BSE or religious issues. In addition, it is well known that the Sepoy Mutiny of 1857 was at least in part triggered by rumors that new British Enfield rifle cartridges were greased with animal fat from cows and pigs, thus offending both Hindus and Moslems. Hence, some consumers may wish to avoid such animal-fat products.

SINEs

Short interspersed elements (SINEs) reside within almost every genome that has been studied to date. Most SINEs have amplified in the past 65 million years and are thought to have been spread throughout each genome via an RNA-mediated duplication process termed retroposition. P. L. Deininger, M. A. Batzer, Evolution of retroposons, Evol. Biol. 27 (1993) 157-196. Because each of the SINE families within the different genomes was derived independently, every mammalian order has a significant number (in excess of 100,000) of characteristic mobile elements.

PCR Terminology

In a polymerase chain reaction (PCR), a predetermined DNA sequence (of a genome) from a DNA sample is multiplied ("amplified") many times to produce a resultant product in which the concentration of the predetermined sequence is greatly increased relative to the concentration in the original DNA sample. This process facilitates detection of the presence of the predetermined DNA sequence (also referred to hereinafter at times as the "sequence of interest"). The amplified sequence in PCR typically contains the DNA sequence of interest flanked at each end by another short sequence. The total amplified sequence is termed an amplicon. The amplicon may be represented as A-X-B-Y-C, where B=the sequence of interest, A=a flanking sequence, C=another flanking sequence, and X and Y are nucleotide sequences. Sequences complementary to A and C, i.e., A' and C', are known as primers; A' is the "forward" primer and C' is the "reverse" primer. The sequence of regions A through C is chosen so that the region B can be amplified using the primers A' and C' having sequences complementary to regions A and C. At times hereinafter, when the sequence of interest B is a SINE, such an amplicon A-B-C is said to be representative of SINE B.

A primer is a reagent that facilitates PCR. Primers are short segments of DNA which are complementary to the two segments of DNA within a strand of DNA that flank the DNA sequence which is to be copied from the strand of DNA (i.e., amplified); in PCR they bind ("anneal") to the DNA sequence which is to be copied. Primers can be specific for a known DNA sequence or can be nonspecific in which case they bind to many genetic sequences. The present invention is concerned primarily with specific primers. More than one primer set can usually be designed for a given sequence of interest. Various constraints and trade-offs govern design and selection of primers.

The copy number is a measure of the number of copies of a given DNA sequence found in a given kind of DNA sample. When the copy number is high, a PCR will produce a higher concentration of the given DNA sequence than when the copy number is low. Detection of a sequence with a high copy number is therefore easier.

The size (length) of an amplicon is measured in terms of base pairs (bp). When a DNA sequence is degraded or truncated, PCR may be unsuccessful. It has been shown that selection of a smaller amplicon, if possible, helps to address this problem, since PCR product yield is inversely correlated to amplicon length. See A. K. Lindquist, P. K. Magnusson, J. Balciuniene, C. Wadelius, E. Lindholm, M. E. Alarcon-Riquelme, U. B. Gyllensten, Chromosome-specific panels of tri- and tetranucleotide microsatellite markers for multiplex fluorescent detection and automated genotyping: evaluation of their utility in pathology. Genome Res. (1996) 6:1170-1176; A. Beckmann, U. Vogt, N. Huda, K. S. Zänker, B. H. Brandt, Direct-Double-Differential PCR for Gene Dosage Quantification of c-myc, Clin. Chem. (1999) 45:141-143.

SUMMARY OF THE INVENTION

Accordingly, it is an object of the present invention to provide assay methods for both detecting qualitatively and also quantitating ruminant-source material in animal feed and pork material in foods.

It is a further object of the present invention to provide assay methods for both detecting qualitatively and also quantitating beef and chicken material in foods of mixed or complex sources. Additionally, it is an object of the invention to provide assay methods applicable to lipsticks and other materials that may contain material from an objectionable or undesired species source.

It is a further object of the present invention to provide primers, probes, and other products adapted to carrying out the foregoing assay methods.

It is a further object of the present invention to provide assay methods for the foregoing purposes that do not require additional processing steps beyond PCR, for example, restriction endonuclease digestion or hybridization for scoring, as in the previously cited assays of Meyer et al. (1995), Bellagamba et al. (2001), and Tartaglia et al. (1998). In addition, it is an object to avoid need for special expertise and expensive special equipment, such as automated DNA sequencers, as in the previously cited assays of Partis et al. (2000) and Bellagamba et al. (2001). It is an object to minimize the cost of performing the assays and to permit laboratories with only average resources to be able to perform the assays.

It is a further object of the present invention to improve the low range detection limits of the assays by at least one order of magnitude over that of previously reported assays in this field.

It is a further object of the present invention to provide assays using less starting DNA template materials than previously reported assays and assays less sensitive to degraded DNA templates than previously reported assays in this field.

These and other objects of the invention are realized by a family of assays based on PCR amplification of short interspersed elements (SINEs) and agarose gel electrophoresis, with probes and primers specially developed for use in these assays. The assays use SINEs as markers to identify the DNA from the species, genus, family, or order of interest, thereby providing specific genomic tags that can be used in conjunction with PCR to amplify specific subsets of genomic sequences unique to the genome or species of interest from mixed-DNA sources. During intra-SINE PCR, primers developed for the assays act within the core body of the SINE to amplify multiple copies of the element of interest and generate a homogeneous product composed entirely of the repeat core unit DNA sequences characteristic of the genome being amplified. The primers were designed and selected with a view to obtaining short-length amplicons to improve accuracy of detection, especially with degraded samples containing a low copy number of DNA sequences of interest.

First, qualitative analyses were performed by inspection of the results of electrophoresis on agarose gel containing ethidium bromide. Second, SYBR Green UV fluorescence detection was used in conjunction with the species-specific intra-SINE PCR to provide a highly quantitative analysis. Third, TaqMan chemistry was used for quantitation instead of SYBR Green-based detection. While fluorescence detection is a preferred mode of quantitation, other forms of tagging the SINE of interest can be used for such detection (e.g., radioactive tagging).

In each case, the assay comprises four basic steps: First, a DNA-containing sample of feed or food to be analyzed is provided. Second, the DNA is extracted or isolated using standard (i.e., conventional) means. Third, PCR amplification of predetermined genomic DNA sequences occurs. The sequences are selected to accomplish the objects of the invention, as described in greater detail below. The sequences selected are SINEs unique to the animal species or family, etc. of interest. The primers are selected to provide small amplicons. The third step results in an amplified DNA product. Fourth, the amplified DNA product is compared with a reference, first using electrophoresis on agarose gel containing ethidium bromide. This provides a qualitative or screening test to detect the DNA of interest. Then SYBR Green fluorescence detection is used where quantitation is required. TaqMan quantitation is also described hereinafter.

Three species-specific assays are described: cow, pig, and chicken; an assay for ruminant species (the various species that are members of the sub-order Ruminata) as a whole is also described. Using SYBR Green-based detection, the minimum effective quantitation levels were 0.1, 0.01, 5, and 1 pg of starting DNA template using the bovine, porcine, chicken, and ruminant species-specific SINE-based PCR assays of the invention, respectively. Background cross-amplification with DNA templates derived from 14 other species was negligible. Species specificity of the PCR amplicons was further tested and demonstrated by measuring the ability of the assays to accurately detect trace quantities of species-specific DNA from mixed (complex) sources. Bovine DNA was detected at 0.005% (0.5 pg), porcine DNA was detected at 0.0005% (0.05 pg), and chicken DNA was detected at 0.05% (5 pg) in a 10-ng mixture of bovine, porcine, and chicken DNA templates. Six commercially purchased meat products were also tested using these assays. The SINE-based PCR methods reported here were shown to be species-specific, and highly sensitive.

Kits are also described for assaying food and feed samples in accordance with the foregoing processes. The kits comprise a polymerase and buffer, and primers suitable for a PCR on the pertinent amplicon.

DETAILED DESCRIPTION

The SINEs of Interest

As previously indicated, the SINEs to be amplified by PCR are selected to uniquely identify the species, genus, etc. of interest, i.e., the subject of the assay. That is, each SINE of interest is selected from a genomic subset common to members of the particular type of animal that is the target of the given assay. But this SINE is one not found in genomes of other types of animal that are non-targets of the given assay.

Figure 1:
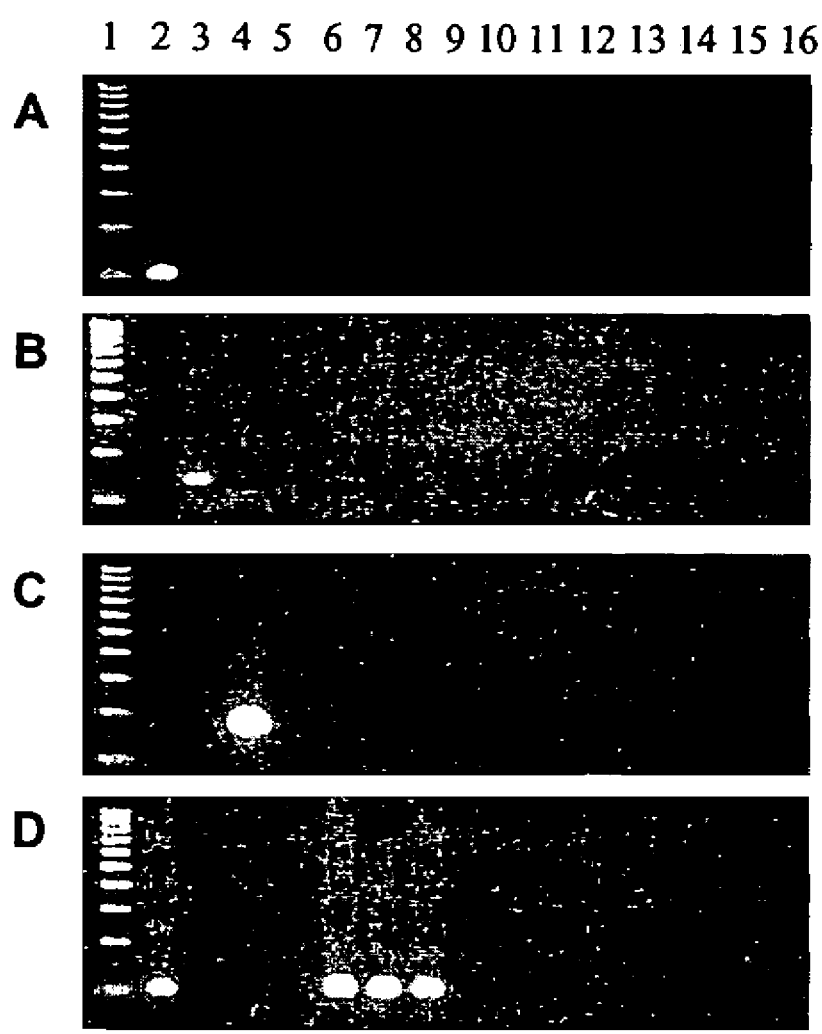
FIG. 1 is a chromatography display for the assays of the invention, showing UV fluorescence visualization of results of gel chromatography of: (A) the bovine-specific assay, (B) the porcine-specific assay, (C) the chicken-specific assay, and (D) the ruminant species assay.

Bovine SINE families such as Bov-tA, Bov-A, and Bov-B are common to all ruminant members of the order Artiodactyla such as shown when using the invention's Bov-tA2 ruminant assay (illustrated in FIG. 1D). See C. Jobse, J. B. Buntjer, N. Haagsma, H. J. Breukelman, J. J. Beintema, J. A. Lenstra, Evolution and recombination of the bovine DNA repeats, J. Mol. Evol. 41 (1995) 277-283. But these elements have also undergone recombination events throughout bovine evolution such that some sequence variants have formed satellites of the original SINE families. Some of these satellites, such as the 1.711B bovine repeat (Gen-Bank No. V00116) used in the bovine (beef) assay of the present invention, emerged after the radiation of the Bovidae approximately 5-15 million years ago and are absent from other ruminant species (see FIG. 1A). See Jobse et al. (1995). Therefore, such elements can advantageously be used to distinguish beef samples from other ruminant-derived samples. The 1.711B bovine repeat is thought to occupy 7.1% of the bovine genome. R. E. Streeck, A multicopy insertion sequence in the bovine genome with structural homology to the long terminal repeats of retroviruses, Nature 298 (1982) 767-768.

The porcine SINE PRE-1 used in the porcine assay of the invention (GenBank No. Y00104) is present in the common domestic pig, Sus scrofa, and other members of the Suidae family, but is absent from other genomes (see FIG. 1B). The PRE-1 SINE sequence reportedly diversified at least 43.2 million years ago and has about 100,000 copies per genome. See D. S. Singer, L. J. Parent, R. Ehrlich, Identification and DNA sequence of an interspersed repetitive DNA element in the genome of the miniature swine, Nucleic Acids Res. 15 (1987) 2780; H. Yasue, Y. Wada, A swine SINE (PRE-1 sequence) distribution in swine-related animal species and its phylogenetic analysis in swine genome, Anim. Genet. 27 (1996) 95-98. Although, technically speaking, this assay detects members of the Suidae family, rather than just the common domestic pig Sus scrofa, the distinction is immaterial since only the common domestic pig is used for commercial meat purposes and, also, any member of the Suidae family is an "unclean" animal proscribed by the Bible (because, although hoofed, they do not chew the cud).

The CR1 family of SINEs reportedly has six sub-families designated A through F. See T. L. Vandergon, M. Reitman, Evolution of chicken repeat 1 (CR1) elements: evidence for ancient subfamilies and multiple progenitors, Mol. Biol. Evol. 11 (1994) 886-898. The chicken assay of this invention was designed in the CR1 SINE subfamily "C" (Gen-Bank No. X03517). This SINE is present in the chicken genome, but it is absent from other avian genomes such as duck (see FIG. 1C) and dove. See W. E. Stumph, P. Kristo, M. Tsai, B. W. O'Malley, A chicken middle-repetitive DNA sequence which shares homology with mammalian ubiquitous repeats, Nucleic Acids Res. 9 (1981); T. L. Vandergon, M. Reitman, Evolution of chicken repeat 1 (CR1) elements: evidence for ancient subfamilies and multiple progenitors, Mol. Biol. Evol. 11 (1994) 886-898.

Primer Design and PCR Amplification

DNA sequences from bovine, see C. Jobse, J. B. Buntjer, N. Haagsma, H. J. Breukelman, J. J. Beintema, J. A. Lenstra, Evolution and recombination of the bovine DNA repeats, J. Mol. Evol. 41 (1995) 277-283; S. Kostia, M. Ruohonen-Lehto, R. Vainola, S. L. Varvio, Phylogenetic information in inter-SINE and inter-SSR fingerprints of the artiodactyla and evolution of the Bov-tA SINE, Heredity 84 (2000) 37-45; R. E. Streeck, A multicopy insertion sequence in the bovine genome with structural homology to the long terminal repeats of retroviruses, Nature 298 (1982) 767-768; porcine, see D. S. Singer, L. J. Parent, R. Ehrlich, Identification and DNA sequence of an interspersed repetitive DNA element in the genome of the miniature swine, Nucleic Acids Res. 15 (1987) 2780; H. Yasue, Y. Wada, A swine SINE (PRE-1 sequence) distribution in swine-related animal species and its phylogenetic analysis in swine genome, Anim. Genet. 27 (1996) 95-98; and chicken, see W. E. Stumph, P. Kristo, M. Tsai, B. W. O'Malley, A chicken middle-repetitive DNA sequence which shares homology with mammalian ubiquitous repeats, Nucleic Acids Res. 9 (1981) 5383-5397; T. L. Vandergon, M. Reitman, Evolution of chicken repeat 1 (CR1) elements: evidence for ancient subfamilies and multiple progenitors, Mol. Biol. Evol. 11 (1994) 886898, genomes were subjected to computational analysis. This was done using the Repeat Masker server at the University of Washington to identify SINEs contained within those genomes.

Oligonucleotides were designed using either Primer3 software (Whitehead Institute for Biomedical Research, Cambridge, Mass.) or Primer Express software (Applied Biosystems, Inc.) and purchased from MWG Biotech, Inc., or Sigma-Genosys, Inc. Each primer pair was evaluated for species specificity and sensitivity using standard PCR and agarose gel electrophoresis. Only those oligonucleotide pairs meeting the previously discussed (see objects of invention) criteria were selected for further analysis (see Tables 1 and 2). The SYBR Green PCR core reagent kit was purchased from Applied Biosystems, Inc. (SYBR is a registered trademark of Molecular Probes, Inc.).

Those skilled in the art will appreciate that some variations or molecular manipulations of the primers described will also serve effectively in a PCR of the SINEs of interest. For example, adding or deleting one or a few bases from the primer or shifting its position slightly relative to the SINE of interest will provide an equivalent of the described primer. Thus, subsets and supersets of the sequences identified for primer use should be considered equivalents thereof, as should substantially overlapping sets. It is considered that the invention extends to such modifications of the primers described herein.

PCR conditions were optimized for each assay with regard to annealing temperature and concentrations of $MgCl_2$ and oligonucleotide primers. Quantitative PCRs were carried out in 50 µl using 1×SYBR Green buffer, 1 mM dNTPs, 3.0 mM $MgCl_2$, and 1.25 units AmpliTaq Gold® DNA polymerase as recommended by the supplier (Applied Biosystems, Norwalk, Conn.). The concentrations of oligonucleotide primers used were 0.3 µM for the bovine assay and 0.2 µM each for the porcine, chicken, and ruminant PCR-based assays. Each sample was subjected to an initial denaturation of 12 min at 95° C. to activate the AmpliTaq Gold, followed by 40 amplification cycles of denaturation at 95° C. for 20 s and either 55° C. to anneal for 45 s and 30 s of extension at 60° C. (bovine, chicken, and ruminant assays) or 63° C. for 1 min to anneal and extend (porcine assay). Each reaction contained 49 µl of PCR reagent mix (master mix) and 1 µl of DNA template. Quantitative PCR experiments were performed using an ABI Prism 7000 sequence detection system (Applied Biosystems, Inc.).

Conventional PCRs for agarose gel detection were carried out in 25 µl using 2 ng of DNA template, 1× PCR buffer II (Applied Biosystems, Inc.), 0.2 mM dNTPs, 1.5 mM $MgCl_2$, 1 unit Taq DNA polymerase, and the same oligonucleotide concentrations as described above. Each sample was subjected to an initial denaturation of 1 min at 95° C., followed by 30 amplification cycles of denaturation at 95° C. for 30 s and either 55° C. to anneal for 30 s and 30 s of extension at 72° C. (bovine, chicken, and ruminant assays) or 63° C. for 1 min to anneal and extend (porcine assay). In the porcine assay, using "hot-start PCR" (automatic with AmpliTaq Gold) and an annealing/extension temperature of 63° C. or higher was critical to assay specificity.

DNA Samples

DNAs from cow (*Bos taurus*), horse (*Equus caballus*), sheep (*Ovis aries*), antelope (*Antilocapra americana*), dog (*Canis familiaris*), cat (*Felis catus*), and rabbit (*Oryctolagus cuniculus*) were obtained by tissue and blood extraction using the Wizard Genomic DNA Purification kit (Promega) and from samples provided by the Louisiana State University School of Veterinary Medicine. Chicken (*Gallus gallus*) DNA was extracted from blood using the QIAamp DNA Blood Mini Kit (Qiagen, Inc.). DNAs from pig (*Sus scrofa*), deer (*Odocoileus virginianus*), duck (*Anas discors*), rat (*Rattus norvegicus*), and mouse (*Mus musculus*), and from commercial food products were prepared from tissue with proteinase K digestion followed by phenol:chloroform extraction and ethanol precipitation. See W. M. Strauss, in: Current Protocols in Molecular Biology, Wiley, New York,

TABLE 1

Repetitive elements and amplicon sizes for intra-SINE PCR detection assays

| Common name | Order | Family | Genus, species | Repeat element | PCR amplicon size (bp) |
| --- | --- | --- | --- | --- | --- |
| Cow | Artiodactyla | Bovidae | *Bos taurus* | 1.711B bov. rpt. | 98 |
| Pig | Artiodactyla | Suidae | *Sus scrofa* | PRE-1 SINE | 134 |
| Chicken | Galliformes | Phasianidae | *Gallus gallus* | CR1 SINE, subf. "C" | 169 |
| Ruminants | Artiodactyla | N/A | N/A | Bov-tA2 SINE | 100 |

TABLE 2

Oligonuclotide primers for intra-SINE-based PCR detection assays

| Assay | Forward primer | Reverse primer |
| --- | --- | --- |
| Bovine | 5' TTTCTTGTTATAGCCCACCACAC 3' (SEQ ID NO:1) | 5' TTTCTCTAAAGGTGGTTGGTCAG 3' (SEQ ID NO:2) |
| Porcine | 5' GACTAGGAACCATGAGGTTGCG 3' (SEQ ID NO:3) | 5' AGCCTACACCACAGCCACAG 3' (SEQ ID NO:4) |
| Chicken | 5' CTGGGTTGAAAAGGACCACAGT 3' (SEQ ID NO:5) | 5' GTGACGCACTGAACAGGTTG 3' (SEQ ID NO:6) |
| Ruminants | 5' CAGTCGTGTCCGACTCTTTGT 3' (SEQ ID NO:7) | 5' AATGGCAACACGCTTCAGTATT 3' (SEQ ID NO:8) |

1998, pp. 2.2.1-2.2.3. Human DNA (HeLa cell line ATCC CCL2) isolations were performed using Wizard genomic DNA purification (Promega). Extracted DNA was stored in 10 mM Tris/0.1 mM EDTA (TLE), quantified spectrophotometrically, and then serially diluted 10-fold in TLE such that concentrations from 10 ng to 0.01 pg were assayed in triplicate using PCR.

Assays

Verification Tests

First a series of assays was performed to determine the quantitation range for each of the four SINEs of Table 1, and these results are shown in FIGS. 2A through 2D. Then a series of assays was performed to determine the cross-amplification of DNA templates derived from each of these and various other species. These results are shown in FIGS. 3A through 3D.

For the purpose of these tests, a number of multi-species DNA mixtures were prepared, as shown in Table 3.

the threshhold cycle plotted on the y axis. A tenfold dilution series of the bovine DNA was carried out. Then the fluorescent signal produced by the tenfold dilution series was plotted by means of three replicates ±1 standard deviation. The $R^2$ value is 99-100%. Analyses of the species in the DNA mixtures of Table 3 are plotted as open triangles in FIG. 2A along the standard curve as the mean of three replicates ±1 standard deviation.

Figure 2:
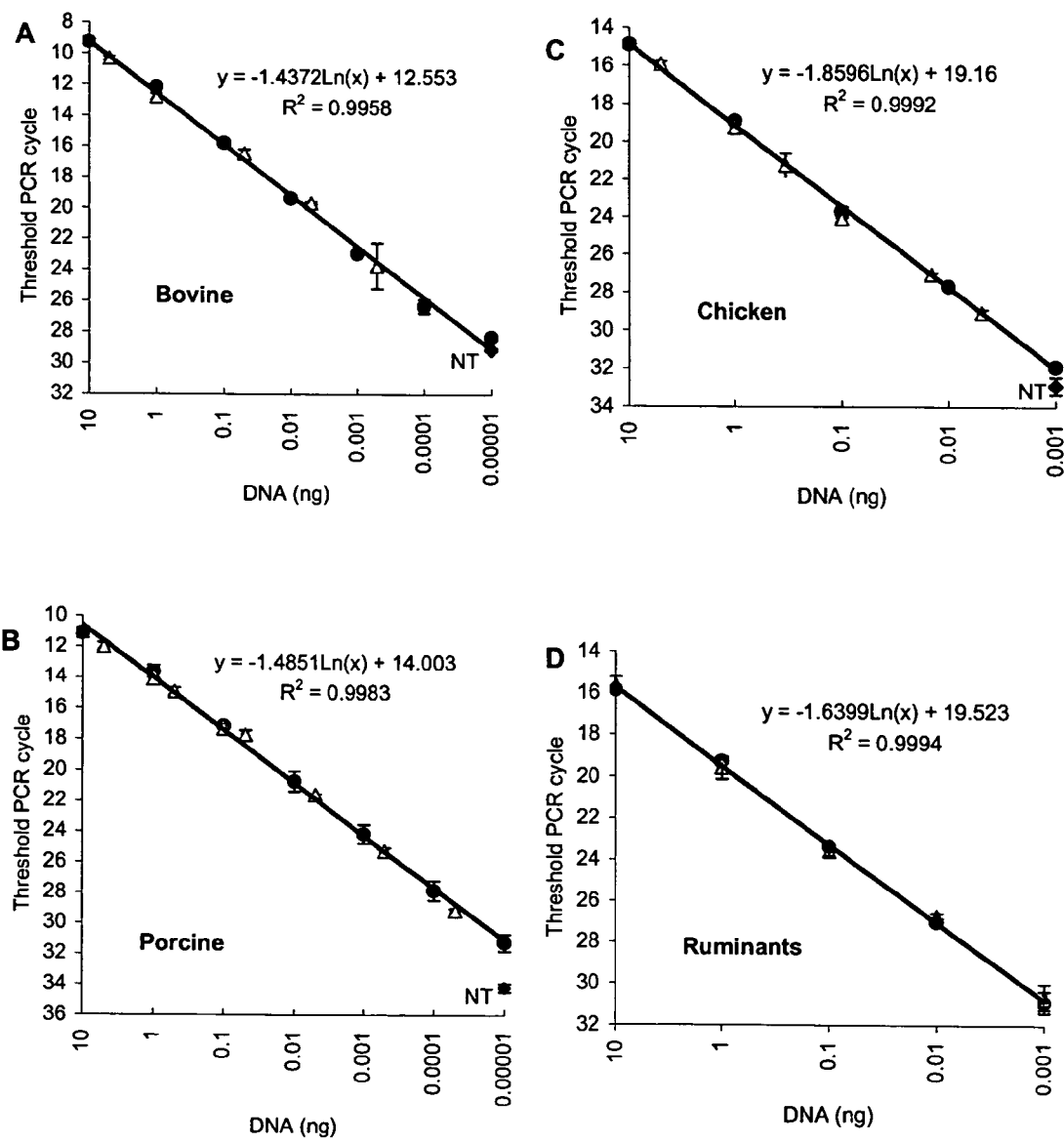
FIG. 2 shows the quantitation range for the four assays of the invention: (A) the bovine-specific assay, (B) the porcine-specific assay, (C) the chicken-specific assay, and (D) the ruminant species assay.

The bovine assay based on the 1.711B bovine repeat had a linear quantitation range of 10 to 0.0001 ng (0.1 pg), or $10^6$, as shown by the standard curve (see FIG. 2A). The mean value of the negative template control (NT) was 29.1±0.1 and was not significantly different from the lowest value tested (0.00001 ng or 0.01 pg). This assay detected the known values of bovine DNA within mixed-DNA samples from 50% (5 ng) to 0.005% (0.5 pg) as indicated by the triangles on the standard curve. A total of 10 ng of DNA template was used in each test. Background cross-amplification was detected in trace amounts only from rabbit (*Or. cuniculus*) and dog (*C. familiaris*) DNA templates, following 26 cycles of PCR when

TABLE 3

Composition of Mixed DNA Samples

|  | Bovine | | Porcine | | Chicken | | Total template | |
| --- | --- | --- | --- | --- | --- | --- | --- | --- |
|  | DNA ng | (%) | DNA ng | (%) | DNA ng | (%) | DNA ng | (%) |
| Bovine mix | | | | | | | | |
| 1 | 5 | (50) | 5 | (50) | 0 | (0) | 10 | (100) |
| 2 | 1 | (10) | 0* | (0) | 0* | (0) | 10* | (100) |
| 3 | 0.05 | (0.5) | 7 | (70) | 2.95 | (29.5) | 10 | (100) |
| 4 | 0.005 | (0.05) | 7 | (72) | 2.795 | (27.95) | 10 | (100) |
| 5 | 0.0005 | (0.005) | 7.22 | (72.2) | 2.7795 | (27.795) | 10 | (100) |
| Porcine Mix | | | | | | | | |
| 1 | 5 | (50) | 5 | (50) | 0 | (0) | 10 | (100) |
| 2 | 4.5 | (45) | 1 | (10) | 4.5 | (45) | 10 | (100) |
| 3 | 4.5 | (45) | 0.5 | (5) | 5 | (50) | 10 | (100) |
| 4 | 4.95 | (49.5) | 0.1 | (1) | 4.95 | (49.5) | 10 | (100) |
| 5 | 4.95 | (49.5) | 0.05 | (0.5) | 5 | (50) | 10 | (100) |
| 6 | 4.995 | (49.95) | 0.005 | (0.05) | 5 | (50) | 10 | (100) |
| 7 | 4.9995 | (49.995) | 0.0005 | (0.005) | 5 | (50) | 10 | (100) |
| 8 | 4.99995 | (49.9995) | 0.00005 | (0.0005) | 5 | (50) | 10 | (100) |
| Chick. mix | | | | | | | | |
| 1 | 2.5 | (25) | 2.5 | (25) | 5 | (50) | 10 | (100) |
| 2 | 4.5 | (45) | 4.5 | (45) | 1 | (10) | 10 | (100) |
| 3 | 4.75 | (47.5) | 4.75 | (47.5) | 0.5 | (5) | 10 | (100) |
| 4 | 4.95 | (49.5) | 4.95 | (49.5) | 0.1 | (1) | 10 | (100) |
| 5 | 4.9925 | (49.925) | 4.9925 | (49.925) | 0.015 | (0.15) | 10 | (100) |
| 6 | 4.9975 | (49.975) | 4.9975 | (49.975) | 0.005 | (0.05) | 10 | (100) |

*Ovine and deer DNA at 4.5 ng each (45% each).

Bovine Assay Quantitation Range and Cross-amplification

After 30 cycles of conventional PCR, amplicons were chromatographed on a 2% agarose gel that contained ethidium bromide and then visualized using UV fluorescence. The results appear in FIG. 1A, where Lane 1 is a 100 bp ladder and Lane 2 is the cow DNA. The empty lanes (lanes without any bands for PCR product) are lanes: (3) pig, (4) chicken, (5) horse, (6) sheep, (7) deer, (8) antelope, (9) rabbit, (10) duck, (11) dog, (12) cat, (13) rat, (14) mouse, (15) human, (16) NTC (no-template control). The empty lanes show the insensitivity of this assay to various non-bovine species.

FIG. 2A shows the quantification range for the assay, using SYBR Green fluorescence detection. The PCR cycle at which the fluorescent signal crosses the baseline is considered to be tested with an equivalent amount of DNA (2 ng) (see FIG. 3A). Therefore, cross-species amplification does not limit the effective quantitation range of this assay when testing DNA samples from complex (mixed) sources.

The criterion that the PCR cycle at which the fluorescent signal crosses the baseline is considered to be the threshhold cycle plotted on the y axis, as described above, is used for all quantitative assays described hereinafter. That concept of threshhold cycle is used as the quantification measure for all of the quantitative PCR assays of the invention, and also in the claims.

Porcine Assay Quantitation Range and Cross-amplification

After 30 cycles of conventional PCR, amplicons were chromatographed on a 2% agarose gel that contained ethidium bromide and then visualized using UV fluorescence. The results appear in FIG. 1B, where Lane 1 is a 100 bp ladder and Lane 3 is the pig DNA. The empty (no band) or substantially empty (very faint band) lanes are lanes: (2) cow, (4) chicken, (5) horse, (6) sheep, (7) deer, (8) antelope, (9) rabbit, (10) duck, (11) dog, (12) cat, (13) rat, (14) mouse, (15) human, (16) NTC (no-template control). The empty lanes show the insensitivity of this assay to various non-porcine species.

FIG. 2B was developed to show the quantitation range for the intra-PRE-1 SINE of the porcine-specific assay in a manner similar to that described above for the bovine assay. The porcine intra-PRE-1 SINE-based PCR assay had a linear quantitation range of 10 to 0.00001 ng (0.01 pg), or $10^7$, as shown by the standard curve (see FIG. 2B). The mean value of the negative control was 34.2±0.3 and was significantly different from 31.3±0.6 at the 0.01 pg level (p=0.0037). This assay detected the known values of porcine DNA within mixed-DNA samples from 50% (5 ng) to 0.0005% (0.05 pg) as indicated by the triangles on the standard curve.

Figure 3:
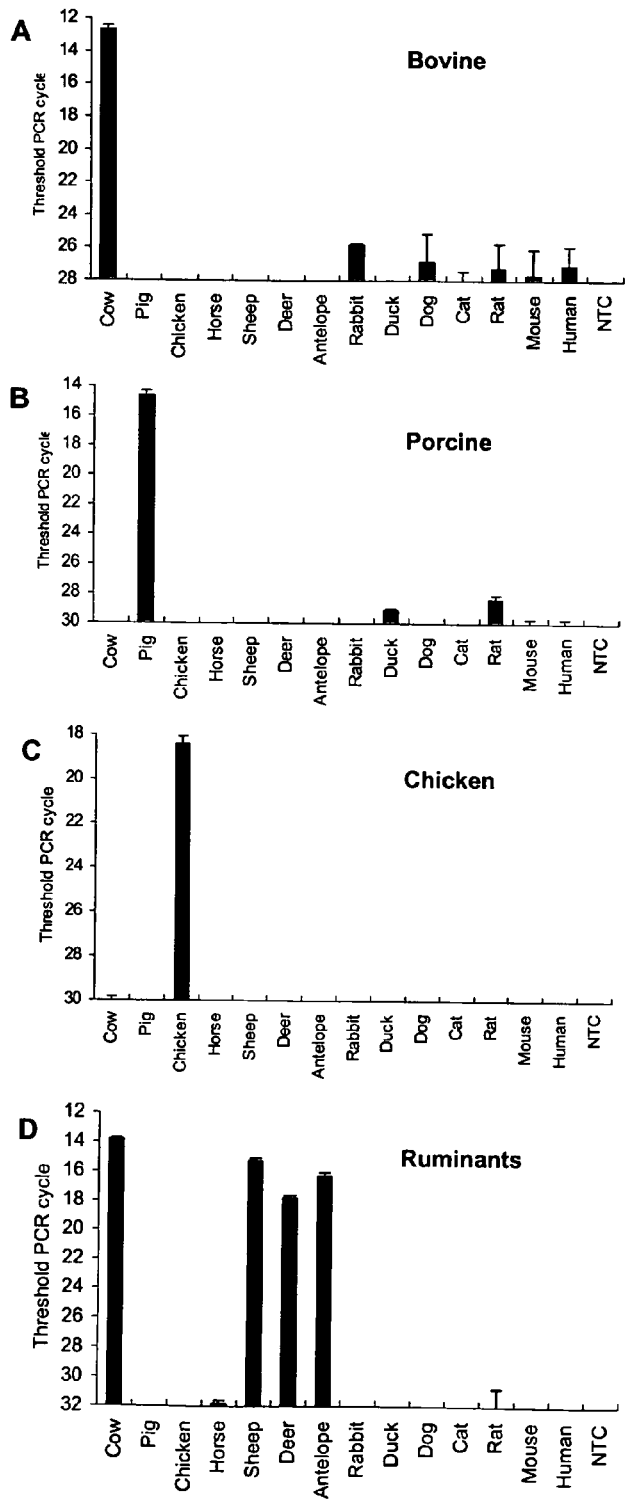
FIG. 3 shows cross amplification of DNA templates derived from 14 species for the four assays of the invention: (A) the bovine-specific assay, (B) the porcine-specific assay, (C) the chicken-specific assay, and (D) the ruminant species assay.

Background amplification was detected in trace amounts only from duck (*Anas discors*) and rat (*R. norvegicus*) following 29 cycles of PCR when tested with an equivalent amount of DNA template (2 ng) (see FIG. 3B). Therefore, cross-species amplification limits the effective quantitation range of this porcine intra-SINE PCR assay to 0.1 pg when equivalent amounts of duck or rat DNA may be present in the samples. However, when DNA samples derived from most complex sources were tested the effective minimum quantitation range was 0.01 pg. The complex sources of principal interest here include pork, beef, lamb, and chicken, which are the most common meat animals in the United States; horse may be of some lesser interest; duck and rat are not of significant interest as likely adulterants of meat products in the United States.

Chicken Assay Quantitation Range and Cross-amplification

After 30 cycles of conventional PCR, amplicons were chromatographed on a 2% agarose gel that contained ethidium bromide and then visualized using UV fluorescence. The results appear in FIG. 1C, where Lane 1 is a 100 bp ladder and Lane 4 is the chicken DNA. The empty lanes (no bands) are lanes: (2) cow, (3) pig, (5) horse, (6) sheep, (7) deer, (8) antelope, (9) rabbit, (10) duck, (11) dog, (12) cat, (13) rat, (14) mouse, (15) human, (16) NTC (no-template control). The empty lanes show the insensitivity of this assay to various non-chicken species.

FIG. 2C was developed to show the quantitation range for the chicken intra-CR1. Subfamily "C" SINE-based PCR assay in a manner similar to that described above for the bovine assay. The chicken intra-CR1 SINE-based PCR assay had a linear quantitation range of 10-0.005 ng, or 2000-fold, as shown by the standard curve (see FIG. 2C). The mean value of the negative control was 32.9±0.5 and was not significantly different from the lowest value tested (0.001 ng). This assay detected the known values of chicken DNA within mixed-DNA samples from 50% (5 ng) to 0.05% (5 pg), as indicated by the triangles on the standard curve. No amplification was detected from any of the other species tested, making this assay absolutely chicken-specific within its quantitation range (see FIG. 3C).

Ruminant Assay Quantitation Range and Cross-amplification

FIG. 1D is based on the same methodology as FIGS. 1A-C, and shows that the intra-Bov-t-A2 SINE-based PCR ruminant assay, carried out by the same procedure as the preceding cases, detects cow (Lane 2), sheep (Lane 6), deer (Lane 7, and antelope (Lane 8). Lane 1 is a 100 bp ladder and the empty lanes are lanes: (3) pig, (5) horse, (9) rabbit, (10) duck, (11) dog, (12) cat, (13) rat, (14) mouse, (15) human, (16) NTC (no-template control). FIG. 1D thus shows the sensitivity of this assay to four ruminant species and its insensitivity to numerous non-ruminant species.

FIG. 2D was developed to show the quantitation range for the intra-Bov-tA2 SINE-based PCR assay for detection of multiple ruminant species in a manner similar to that described above for the bovine assay. The intra-Bov-tA2 SINE-based PCR assay has a linear quantitation range of 10-0.001 ng ($10^4$) using bovine DNA as shown by the standard curve and also using ovine DNA shown by the triangles superimposed along the standard curve (see FIG. 2D). The combined mean value of the negative control (not shown) was 34.8±0.4 and was significantly different from 30.9±0.5 at the 0.001 ng level (p=0.02). PCR amplification was detected from all ruminant species tested (cow, sheep, deer, and antelope) and no signal was detected from other species (see FIG. 3D). The intra-Bov-tA2 SINE-based PCR assay thus allows sensitive simultaneous quantitation (down to 1 pg of starting DNA template) of DNA derived from various ruminant species in a single assay.

Figure 4:
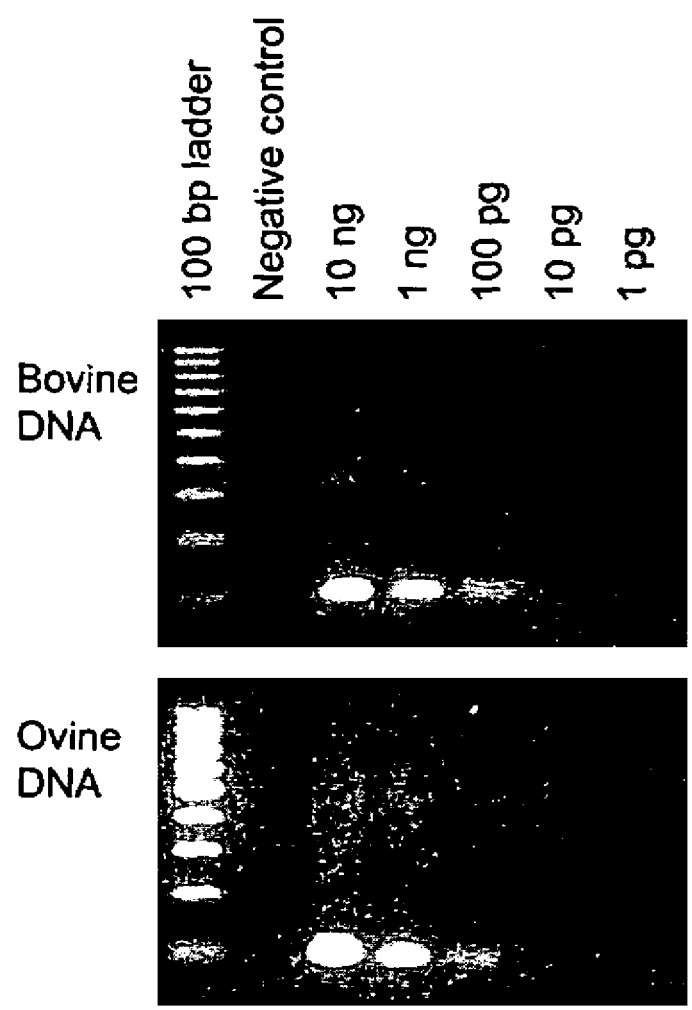
FIG. 4 shows DNA detection showing UV fluorescence visualization of results of gel chromatography of the ruminant assay of the invention as applied to mixed DNA samples containing 1%: (A) bovine DNA, and (B) sheep DNA.

FIG. 4 shows ruminant DNA detection using the intra-Bov-tA2 SINE-based PCR assay at concentrations from 10 ng to 1 pg. Following 30 cycles of conventional PCR using the intra-Bov-tA2 SINE oligonucleotide primers, amplicons were chromatographed on a 2% agarose gel stained with ethidium bromide. Using ruminant DNA standards from both bovine and ovine genomes, the assay detected 100 pg of ruminant DNA, corresponding to 1% in a 10-ng mixed-DNA sample of starting template. This assay thus permits detection, at 100 pg, and rough quantitative estimates to be performed by simple, inexpensive agarose gel electrophoresis as an initial screening tool. It is considered that the data shown in FIG. 4 indicates the utility of the instant ruminant assay for purposes of testing feed material for compliance with government regulations against use of ruminant source protein in feed.

Assay specificity was further evaluated by testing the ability of the assays to accurately detect known trace quantities of species-specific DNA from complex (mixed) templates containing other DNAs. Bovine DNA was detected at 0.005% (0.5 pg), porcine DNA was detected at 0.0005% (0.05 pg), and chicken DNA was detected at 0.05% (5 pg) in a 10-ng mixture of bovine, porcine, and chicken DNA.

Tests on Commercial Meat Samples

After verification of the quantification range of the assays and their specificity, a series of assays were performed on six different meat products purchased at random from local stores. These were ground meat or sausage, as shown in Table 4.

TABLE 4

Contents of six commercially purchased meat samples

| Meat Product | Ingredients (per package label) |
|---|---|
| a. Ground beef | 73% ground beef; 27% fat |
| b. Ground pork | Fresh ground pork; 28% fat |
| c. Ground lamb | Fresh ground lamb; 28% fat |
| d. Pork sausage | Pork, water, green onions, salt, sugar, spices, paprika, granulated garlic, natural flavors |
| e. Chicken sausage | Chicken, green onions, salt, red pepper, black pepper, garlic powder, sugar, paprika |
| f. Mixed pork and beef sausage | Pork, beef, salt, red pepper, black pepper, garlic powder, sugar, paprika |

EXAMPLE 1

Agarose Gel Fluorescence Meat Assays 30 cycles of conventional PCR were carried out using 2 ng of template DNA (extracted by conventional means) from six different commercially purchased meat products. The amplified products were chromatographed on a 2% agarose gel stained with ethidium bromide. The detection was performed in the visualization of FIG. 5A with bovine DNA using the 1.711B bovine repeat assay. The detection was performed in the visualization of FIG. 5B with porcine DNA using the intra-PRE-1 SINE assay. The detection was performed in the visualization of FIG. 5C with chicken DNA using the intra-CR1, subfamily "C" SINE assay. The detection was performed in the visualization of FIG. 5D with ruminant DNA using the intra-Bov-t-A2 assay.

Lanes: (1) 100 bp DNA ladder; (2) negative control; (3) positive control DNA (A, bovine; B, porcine; C, chicken; and D, ovine); (4) ground beef; (5) ground pork; (6) ground lamb; (7) pork sausage; (8) chicken sausage; (9) mixed beef and pork sausage.

As appears from FIGS. 5A-D, each positive control was visualized and no negative control was visualized. Beef showed, as was to be expected, in the ground beef sample and the mixed beef-pork sausage sample. Beef also showed to a slight extent in the chicken sausage sample. Pork showed, as was to be expected, in the ground pork sample and pork sausage, as well as in mixed beef-pork sausage. It also showed in chicken sausage. Chicken showed, as was to be expected, in the chicken sausage. It also showed slightly in the mixed beef-pork sausage. Ruminant showed, as was to be expected, in ground beef, ground lamb, and mixed-beef pork sausage. The agarose gel ethidium bromide assays showed significant contamination (pork) only in the chicken sausage, and showed slight contamination (beef) in the chicken sausage.

Restating the same data in terms of the different meat samples, rather than on an DNA-assay-by-DNA-assay basis, leads to the following conclusions: The ground beef sample contained only beef (FIGS. 5A-D, lane 4). The ground pork sample contained only pork (FIGS. 5A-D, lane 5). The ground lamb contained DNA from a ruminant species and did not contain beef, chicken, or pork (FIGS. 5A-D, lane 6). The pork sausage contained only pork and no beef, chicken, or ruminant species (FIGS. 5A-D, lane 7). The chicken sausage contained chicken, but also appeared to have some beef and pork components (FIGS. 5A-D, lane 8). The mixed sausage contained beef and pork as labeled and also trace amounts of chicken (FIGS. 5A-D, lane 9).

EXAMPLE 2

Quantitative PCR Meat Assays

Figure 6:
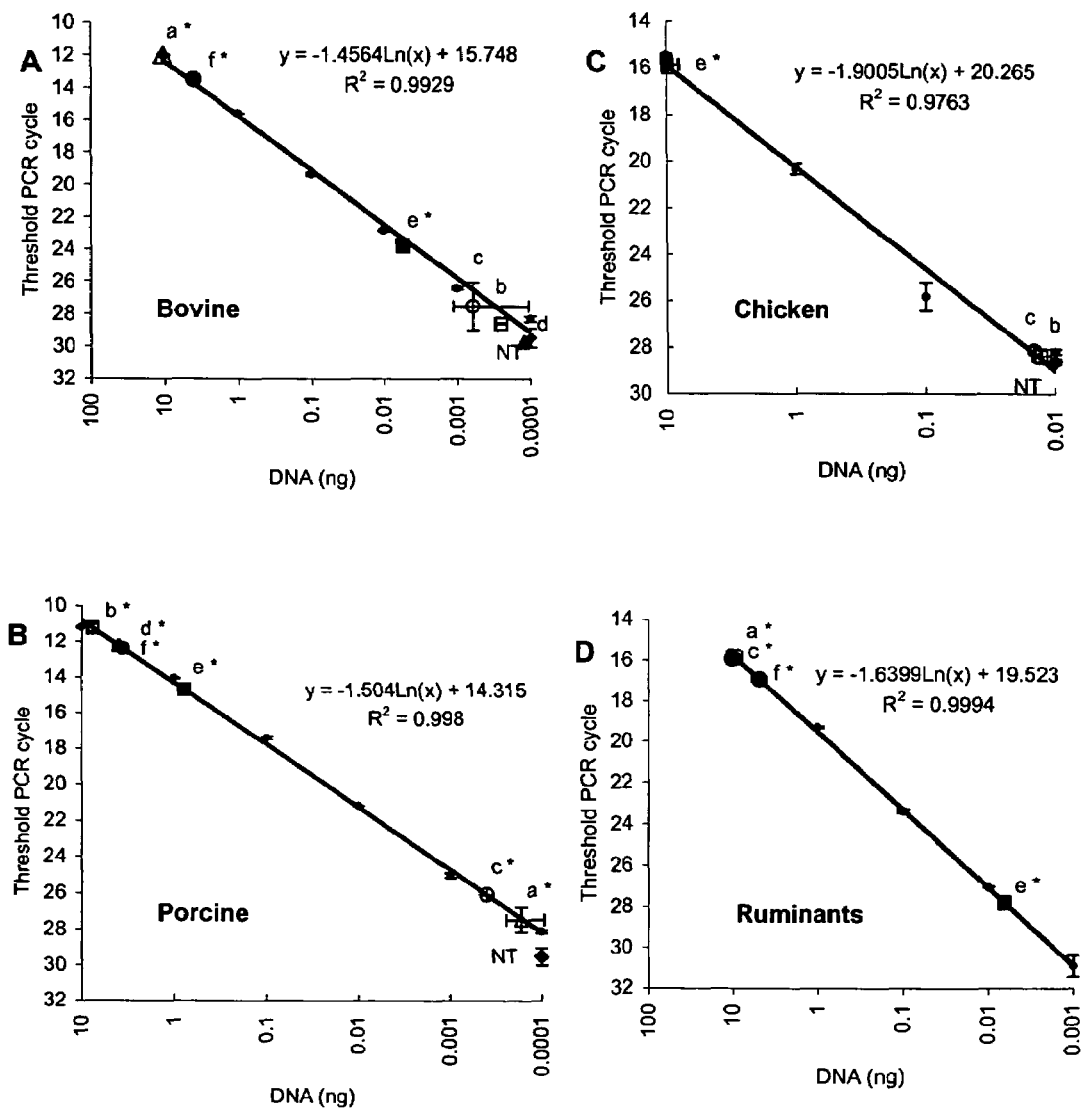
FIG. 6 shows quantitative PCR analysis of complex mixtures from six meat products, using the four assays of the invention: (A) the bovine-specific assay, (B) the porcine-specific assay, (C) the chicken-specific assay, and (D) the ruminant species assay.

Quantitative PCR analysis was undertaken for six meat samples, using the same primers and SYBR Green fluorescence detection. Results are shown in FIG. 6.

In FIGS. 6A through 6D, the six products were labeled as follows: (a) ground beef—open triangles; (b) ground pork—open squares; (c) ground lamb—open circles; (d) pork sausage—filled triangles; (e) chicken sausage—filled squares; (f) mixed beef and pork sausage—filled circles. The PCR cycle at which the fluorescent signal crosses baseline is considered to be the threshold cycle, plotted on the y axis. The fluorescent signal produced by a 10-fold dilution series of (A) bovine, (B) porcine, (C) chicken, or (D) bovine and ovine DNA is plotted as the mean of duplicates ±1 standard deviation, to form a standard curve. DNA (10 ng) from each meat sample was analyzed in duplicate using each of the four quantitative assays. Values were calculated using the standard curves and plotted as the mean with x and y error bars equal to 1 standard deviation. Values significantly different from the no template control are marked with an asterisk (*p=0.05).

The results from Example 2 indicated that both the ground beef sample and the ground lamb sample contained trace amounts of pork, 0.17±0.10 pg (~0.002%) and 0.40±0.00 pg (~0.004%), respectively (see FIG. 6B). These calculated values were in both cases significantly different from the negative control (p=0.05). The mixed sausage sample contained beef and pork in almost equal amounts as indicated on the product label (see FIGS. 6A, 6B and 6D) and did not contain any chicken DNA within the quantitative range of the assay (see FIG. 6C), contrary to the indications of the initial gel-based screening. The chicken sausage contained significant levels of both beef and pork, 5.6±0.0 pg (~0.06%) and 0.77±0.09 ng (~7.7%), respectively, as suggested by the gel-based assay (see FIGS. 6A and 6B).

TaqMan Chemistry

TaqMan chemistry involves use of a probe in PCR as well as use of primers as previously described. The first stage in assay design is to design a suitable primer and probe. The primer is a short piece of genetic material that allows Taq polymerase, an enzyme that catalyses the replication of DNA/RNA, to attach to the DNA segment of interest (such as, here, porcine PRE-SINE 1) and is specific to that sequence (the target). The probe is a specific DNA sequence that will only stick to the piece of target material. Attached to opposite ends of the probe are two fluorescent dye molecules; one is a reporter molecule, the other a quencher molecule. The reporter emits fluorescent light at a specific wavelength, and the quencher absorbs this light. (A typical reporter dye is 6-carboxyfluorescein (FAM), which has its emission spectra quenched due to the spatial proximity of a second fluorescent dye, 6-carboxy-tetramethyl-rhodamine (TAMRA).) This means that when the two molecules are in close proximity, such as at either end of the probe, no light is seen. However, if the two molecules are separated, the reporter molecule will emit light, which will be detected by the machine.

At the beginning of the detection steps, samples are introduced to the TaqMan® equipment, as are the specific primers and probes. If there are regions of sequences present that are specifically detectable by the primers and probe, the primer and probe will attach to the genetic material at respective positions, allowing amplification to occur. The DNA polymerase enzyme recognizes the region where primer is annealed and then continues to make new DNA using the sequence as a template. Once it reaches the point where the probe is annealed, it cleaves the chemical bond between the reporter dye and probe, releasing the reporter molecules. This leads to an increase in the light output, which is detected by the Taqman equipment. As the PCR cycles increase in number, the light intensity increases, too. During the entire amplification process this light emission intensity increases exponentially, the final level being measured by spectrophotometry after termination of the PCR. Because increase of the fluorescence intensity of the reporter dye is achieved only when probe hybridization and amplification of the target sequence has occurred, the TaqMan assay provides a sensitive method to determine the presence or absence of specific sequences. Therefore, TaqMan chemistry has been widely used in diagnostic applications. As previously indicated, however, other forms of tagging are also well known and are capable of use in the assay. For example, other fluorescent dyes exist besides SYBR Green and, also, radioactive tagging can be used here instead of using a fluorescent tag.

EXAMPLE 3

Taq Man Pork Assay

A TaqMan probe for the PRE-1 intra-SINE porcine detection assay was designed: 5'FAM-TTTGATCCCTGGCCT-TGCTCAGTGG-TAMRA 3' (5' FAM-SEQ ID NO:9-TAMRA 3'). The assay of FIG. 6B was then performed with this probe and the results were compared with the SYBR Green-based pork assay of Example 2 and FIG. 6B. The assay sensitivity was, unexpectedly, almost the same. It appears that at least the 5'-FAM reporter molecule typically used with TaqMan-based detection chemistry is not significantly different from SYBR Green in sensitivity.

A second TaqMan probe (using a non-TAMRA quencher) and primer set was designed for a PRE-1 intra-SINE assay. This detection system was approximately as sensitive as the SYBR Green-based detection system in terms of linear quantitation of a pig DNA sample. But this detection system is considered a less preferred mode than SYBR Green-based detection because of cross-species amplification leading to a higher background signal from other species with mixed samples. While this detection system has some utility, it is considered less preferable than the system of Ex. 3. This second TaqMan porcine assay used the following primers and probe:

```
Forward primer:                    (SEQ ID NO:10)
5' GGCCTTGCTCAGTGGGTTAA 3'

Reverse primer:                    (SEQ ID NO:11)
5' GGGATCCAAGCCACATCTGT 3'

Probe:
5' FAM-ACAGCTCACGGCAACGCCGG-BHQ1 3'
(5'FAM-SEQ ID NO:12-BHQ(Black HOle Quencher)1 3'
```

EXAMPLE 4

TaqMan Beef, Ruminant, Chicken Assays

TaqMan probes are designed for the 1.711B bovine repeat, Bov-tA2, and CR1 subf. "C" SINEs, respectively. The assays of FIGS. 6A, C, and D are performed with these probes and the results are compared with the SYBR Green-based assays of Ex. 2 and FIGS. 6A, C, and D. The assay sensitivity is approximately the same.

An implementation of these assays, in conjunction with the TaqMan chemistry assay of Ex. 3, is designed for a multicolor multiplex assay of beef, pork, and chicken. The uniformity of each species-specific amplicon in conjunction with fluorophor-specific TaqMan probes makes the combined assays amenable to a multicolor multiplex detection, which is not available with SYBR Green-based detection.

Figure 5:
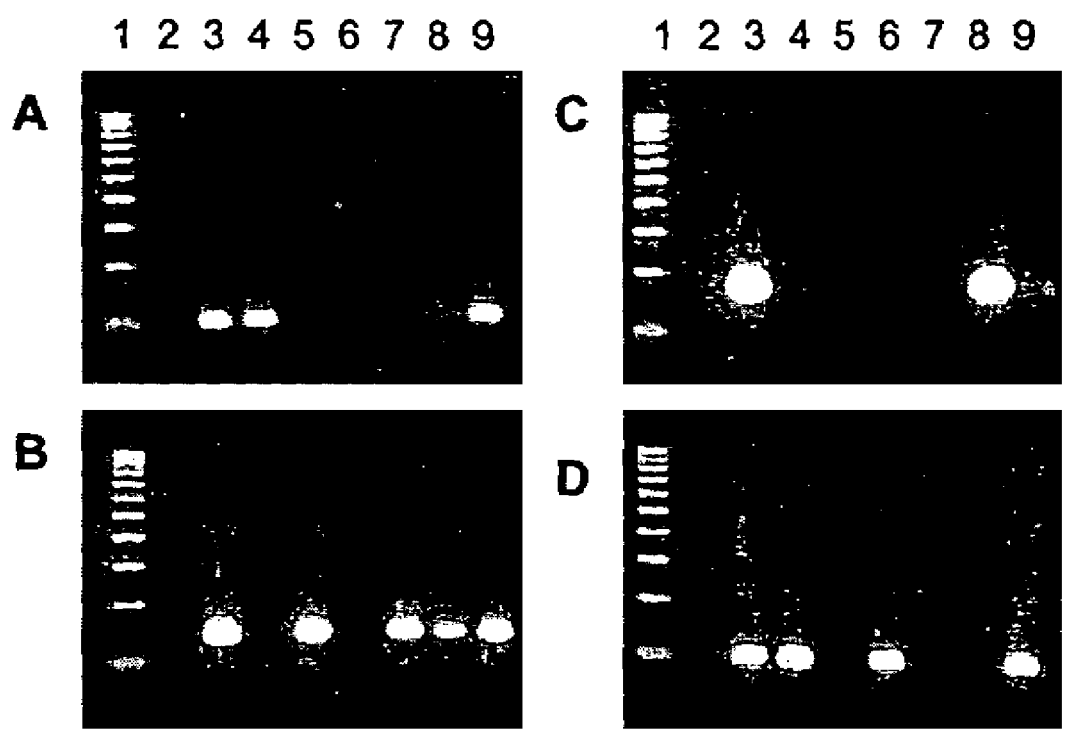
FIG. 5 illustrates UV fluorescence visualization of results of gel chromatography of eight complex meat sample mixtures, using the four assays of the invention: (A) the bovine-specific assay, (B) the porcine-specific assay, (C) the chicken-specific assay, and (D) the ruminant species assay.

It is considered that the ruminant assays of meat samples of FIGS. 5D and 6D provide proxies for a ruminant assay of cattle feed samples, indicating the utility of the ruminant assays for testing compliance with current guidelines and regulations intended to prevent spread of BSE.

EXAMPLE 5

Cattle Feed Assay

Samples A and B of cattle feed containing 25% protein of unknown origin are subjected to the procedures of Example 1. Sample A shows results comparable to those of FIG. 5D. Sample B shows all lanes empty except positive control. It is concluded that sample A contains ruminant-source material, contrary to government regulations, and sample B does not.

EXAMPLE 6

Lipstick Assay

A commercially available lipstick tube containing a lipstick of unknown content is subjected to DNA extraction and the procedures of Example 1. The lipstick shows the presence of material derived from a ruminant species, based on results comparable to those of FIG. 5D.

Evaluation of Data from Verification Tests and Assay Ex. 1-2

First, the assays of Examples 1 and 2 met the objectives of the invention of not requiring process steps such as endonuclease digestion or hybridization for scoring, and they could be performed by simple agarose gel analysis as an initial screening tool. The cost was moderate and no expensive special equipment (such as an automated DNA sequencer) was needed. Addition of SYBR Green-based detection made possible accurate quantitation, as did use of TaqMan chemistry. The assays thus satisfied the object of the invention to provide assays that lent themselves both to inexpensive gel agarose qualitative tests for screening purposes and also to quantitation. The assays also met the objects of short amplicon length, to improve accuracy (especially for degraded DNA templates), and high copy number. It is believed that no other reported assays meet all of these objectives of this invention.

Bovine Assay

The quantitation range of the bovine detection assay was approximately $10^6$, with a minimum effective quantitation level of 0.1 pg of DNA. The detection limits using previously reported methods range from 2.5 pg, see J. H. Calvo, C. Rodellar, P. Zaragoza, R. Osta, Beef- and bovine-derived material identification in processed and unprocessed food and feed by PCR amplification, J. Agric. Food Chem. 50 (2002) 5262-5264, to 250 pg, see T. Matsunaga, K. Chikuni, R. Ranabe, S. Muroya, K. Shibata, J. Yamada, Y. Shinmura, A quick and simple method for the identification of meat species and meat products by PCR assay, Meat Sci. 51 (1999) 143-148; M. Tartaglia, E. Saulle, S. Pestalozza, L. Morelli, G. Antonucci, P. A. Battaglia, Detection of bovine mitochondrial DNA in ruminant feeds: a molecular approach to test for the presence of bovine-derived materials, J. Food Prot. 61 (1998) 513-518; P. Krcmar, E. Rencova, Identification of bovine-specific DNA in feedstuffs, J. Food Prot. 64 (2001) 117-119, of bovine DNA. Thus, the low range detection limit of the intra-SINE-based quantitative bovine PCR assay of this invention exceeds the previously reported assays by a minimum of 25-fold.

Moreover, the previously reported assays do not meet other objectives of the present invention. Thus, Z. Guoli et al.

(1999) and J. H. Calvo et al. (2002) reported PCR assays based on the bovine 1.709 satellite. But both assays were qualitative (gel based) and not quantitative. Furthermore, the 1.709 repeat is estimated to occupy 4.3% of the bovine genome, see C. Jobse et al. (1995), whereas the instant assay uses the 1.711 repeat which is estimated to occupy 7.1% of the bovine genome, and thus has a much higher copy number. The bovine assay of this invention is believed to be the only reported quantitative assay based on genomic repetitive sequences.

Porcine Assay

The intra-SINE-based porcine quantitative PCR assay proved to be even more sensitive than the bovine assay, with a quantitative range of $10^7$ and a minimum effective quantitation level of 0.01 pg. The detection limits previously reported using other methods ranged from 1 pg (0.005% in 20 ng), see Calvo et al. (2001); Tajima et al. (2002), to 250 pg, as in Matsunaga et al. (1999). Thus, the low range detection limit of the instant porcine intra-SINE-based quantitative PCR assay exceeds the currently available assay methods by a minimum of 100-fold.

Chicken Assay

A comparison of the chicken intra-SINE-based quantitative PCR assay to previously reported methods was difficult because the previous studies describing chicken-specific PCR-based quantification assays either did not report a detection limit for poultry, as in Lahiff et al. (2000), or reported a minimum detection limit of 250 pg, as in Matsunaga et al. (1999). The quantitative range of the chicken intra-SINE PCR assay of this invention was approximately 2000-fold, with a minimum effective quantitation level of 5 pg of template, an improvement by a factor of 50 over prior PCR quantitations.

Ruminant Assay

The quantitative range of the ruminant species intra-SINE detection assay of this invention was approximately $10^4$, with a minimum effective quantitation level of 1 pg. The detection limits of previously reported assays for ruminant species detection are similar to those previously reported for bovine detection assays, so that the ruminant assay of this invention exceeds the detection limits of previously reported assays by more than an order of magnitude.

Amplicon Size and DNA Degradation

The size of the PCR amplicons used to detect ruminant, porcine, and chicken DNA in the instant intra-SINE-based quantitative PCR assays are 81 bp (45%), 45 bp (25%), and 32 bp (16%) shorter than those reported by Tajima et al. (2002). The latter assays appear to be based on the next shortest reported PCR amplicons for quantitative assays based on detection of a repetitive genomic sequence. See Table 5. J. H. Calvo et al. (2002) reported a PCR beef assay with an amplicon of 84 bp in length, but the assay was a qualitative gel based assay only, and was based on the 1.709 repeat, which as previously indicated has a much lower copy number than the amplicon of the beef assay of the instant invention. J. H. Calvo et al. (2001) reported a 161 bp amplicon for a pork assay based on an unspecified DNA sequence, which is somewhat shorter in length than the 179 bp amplicon of Tajima, see Table 4, but the Calvo assay was not quantitative. The present quantitative assays therefore should be highly useful contributions to the art as assays for the analysis of samples that contain degraded DNA templates.

TABLE 5

| | Amplicon Sizes (bp) | |
|---|---|---|
| Assay Type | Assay of Invention | Other Assay (min.) |
| Pork | 134 | 179 |
| Beef | 98 | None reported |
| Ruminant | 100 | 181 |
| Chicken | 169 | 201 |

Kits

It is considered that the scope of the invention extends to kits used to practice the assays of the invention. Thus, it is contemplated that the invention would be exploited by marketing kits for DNA quantitation of unknown biological samples, using the principles and procedures described hereinabove. A DNA quantitation kit comprises reagents and DNA control materials. The control contains a predetermined amount of DNA sample of the animal source of interest, suspended in an appropriate salt solution. The reagent mix, often termed a Primer Mix, contains the primers, salts, and other chemicals such as dNTPs, in proportions suitable to obtain the desired results. The following examples illustrate representative kits for practicing embodiments of the invention.

EXAMPLE 7

Kit for Quantitative Assay of Meat for Pork Content

A kit suitable for performing a single assay to quantitate pork presence in a ground meat sample believed to contain some pork comprises PCR tubes, sterile water, sterile TLE, SYBR® Green core reagent kit and porcine DNA controls, and a pair of primers (forward, 5'GACTAGGAACCATGAG-GTTGCG 3' (SEQ ID NO:3); reverse, 5'AGCCTACACCA-CAGCCACAG 3' (SEQ ID NO:4)) that are adapted for amplification of the Pre-1 SINE of the porcine-specific assay of the invention, or else a TaqMan probe that is designed to be so adapted (e.g., 5' FAM-TTTGATCCCTGGCCTTGCT-CAGTGG-TAMRA 3'(5' FAM-SEQ ID NO:9 - TAMRA 3')). The concentrations of each reagent are selected depending on the intended use of the kit. Since the detection range of the porcine assay is $10^7$—from 0.01 pg—dilutions within this range should be selected that bracket the anticipated concentration of porcine DNA in the sample.

It is useful to analyze more than one concentration of the unknown DNA sample. Stock primers are reconstituted in sterile TLE to a concentration of 100 µM. Then, 0.5 ml of working solution of each primer at 10 µM is made by diluting 50 µl of each stock with 450 µl of TLE. This represents a 10× working concentration of each primer for the quantitative PCR assay. PCR tubes, strips or plate as needed are prepared, and a template showing the location of the negative control (TLE), the positive controls (A 10-fold serial dilution of porcine control DNA from 10 ng/µl). 1 µl of DNA template is pipetted into each appropriate well. Then a master mix of all remaining PCR reagents is prepared. 49 µl of master mix is pipetted into each well and is pipetted to make a final PCR reaction volume of 50 µl, as recommended by the manufacturer (SYBR® Green PCR core reagent kit). PCR tubes or plate is placed into the Z-PCR machine. PCR is performed as in Example 2. The amplification analysis is performed using an ABI prism 7,000 sequence detection system (Applied Biosystems, Inc.) or a Bio-Rad i-cycler iQ real-time PCR detection system. A calibration curve is generated from the results for the standard DNA samples.

As used in the claims, determining the presence of a SINE or amplicon representative of the SINE comprises qualitative determination or quantitative determination of such presence, or both. As used in the claims ordinary agarose gel electrophoresis means electrophoresis on an agarose gel without any additional procedural steps, such as endonuclease digestion. As used in the claims, insensitive to presence of material from a given type of animal as source means that the amount (weight, e.g., in pg) detected (or putatively detected) from that type of animal source is not significantly greater than the amount detected for the negative control in the assay.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made.

For example, it is known to use other fluorescent dyes instead of ethidium bromide, and substitution of one of them for ethidium bromide should be considered the substitution of an equivalent. Other forms of tags and tagging (also known as labeling), besides fluorescent dyes, can also be substituted—for example, biotin, a chemiluminescer, enzyme, or a radioisotope. A fluorescent tag can be incorporated into a PCR product by using either a labeled primer or a labeled dUTP, and the two expedients should be considered equivalent. Also, it is known to substitute polyacrylamide gel for agarose gel. In principle, SYBR Green-based or TaqMan chemistry can be used to carry out a qualitative or screening test, but it is considered impractical to do so, at least at present, because of cost considerations and added complexity, relative to gel electrophoresis. At this time, work is being done on other DNA amplification processes to supplement PCR. It is considered that, if and when such further amplification processes become commercially available, they will provide equivalents to use of PCR in this invention.

It should be appreciated that the scope of this invention is not limited to the detailed description of the invention hereinabove, which is intended merely to be illustrative, but rather comprehends the subject matter defined by the following claims.

That which is claimed is:

1. A process for assaying a sample of unknown content to determine the presence of bovine-source material in the sample, said process comprising the steps of:
    (1) extracting a DNA sample from the sample to be assayed;
    (2) adding to the DNA sample a primer pair, said primer pair comprising:
       the sequence of 5' TTTCTTGTTATAGCCCACCACAC 3' (SEQ ID NO: 1); and
       the sequence of 5' TTTCTCTAAAGGTGGTTGGTCAG 3' (SEQ ID NO: 2), whereby a pre-PCR mixture is provided;
    (3) carrying out a polymerase chain reaction (PCR) on the pre-PCR mixture, whereby an amplified DNA product results; and
    (4) determining the presence in the amplified DNA product of a predetermined amplicon representative of 1.711B bovine repeat.

2. The process of claim 1, wherein the step of determining the presence of the predetermined amplicon comprises: performing electrophoresis.

3. The process of claim 1, wherein the step of determining the presence of the predetermined amplicon comprises:
    adding SYBR Green dye in the step of carrying out the polymerase chain reaction;
    subjecting the amplified DNA product to UV to provide a fluorescent signal; and
    then evaluating the fluorescent signal for a PCR cycle at which it crosses a baseline.

4. A process for assaying a sample of unknown content to determine the presence of chicken-source material in the sample, said process comprising the steps of:
    (1) extracting a DNA sample from the sample to be assayed;
    (2) adding to the DNA sample a primer pair, said primer pair comprising:
       the sequence of 5' CTGGGTTGAAAAGGACCACAGT 3' (SEQ ID NO: 5); and
       the sequence of 5' GTGACGCACTGAACAGGTTG 3' (SEQ ID NO: 6), whereby a pre-PCR mixture is provided;
    (3) carrying out a polymerase chain reaction (PCR) on the pre-PCR mixture, whereby an amplified DNA product results; and
    (4) determining the presence in the amplified DNA product of a predetermined amplicon representative of CR 1 repeat.

5. The process of claim 4, wherein the step of determining the presence of the predetermined amplicon comprises: performing electrophoresis.

6. The process of claim 4, wherein the step of determining the presence of the predetermined amplicon comprises:
    adding SYBR Green dye in the PCR amplification step;
    subjecting the amplified product to UV to provide a fluorescent signal; and
    then evaluating the fluorescent signal for a PCR cycle at which it crosses a baseline.

* * * * *

```
                        SEQUENCE LISTING

<160> NUMBER OF SEQ ID NOS: 12

<210> SEQ ID NO 1
<211> LENGTH: 23
<212> TYPE: DNA
<213> ORGANISM: Artificial
<220> FEATURE:
<223> OTHER INFORMATION: Forward Primer for 1.711B bovine repeat

<400> SEQUENCE: 1
tttcttgtta tagcccacca cac                                            23

<210> SEQ ID NO 2
<211> LENGTH: 23
<212> TYPE: DNA
<213> ORGANISM: Artificial
<220> FEATURE:
<223> OTHER INFORMATION: Reverse Primer for 1.711B bovine repeat

<400> SEQUENCE: 2
tttctctaaa ggtggttggt cag                                            23

<210> SEQ ID NO 3
<211> LENGTH: 22
<212> TYPE: DNA
<213> ORGANISM: Artificial
<220> FEATURE:
<223> OTHER INFORMATION: Forward Primer for PRE-1 SINE

<400> SEQUENCE: 3
gactaggaac catgaggttg cg                                             22

<210> SEQ ID NO 4
<211> LENGTH: 20
<212> TYPE: DNA
<213> ORGANISM: Artificial
<220> FEATURE:
<223> OTHER INFORMATION: Reverse Primer for PRE-1 SINE
```

<400> SEQUENCE: 4
agcctacacc acagccacag                                           20

<210> SEQ ID NO 5
<211> LENGTH: 22
<212> TYPE: DNA
<213> ORGANISM: Artificial
<220> FEATURE:
<223> OTHER INFORMATION: Forward Primer for CR1 SINE

<400> SEQUENCE: 5
ctgggttgaa aaggaccaca gt                                        22

<210> SEQ ID NO 6
<211> LENGTH: 20
<212> TYPE: DNA
<213> ORGANISM: Artificial
<220> FEATURE:
<223> OTHER INFORMATION: Reverse Primer for CR1 SINE

<400> SEQUENCE: 6
gtgacgcact gaacaggttg                                           20

<210> SEQ ID NO 7
<211> LENGTH: 21
<212> TYPE: DNA
<213> ORGANISM: Artificial
<220> FEATURE:
<223> OTHER INFORMATION: Forward Primer for Bov-tA2 SINE

<400> SEQUENCE: 7
cagtcgtgtc cgactctttg t                                         21

<210> SEQ ID NO 8
<211> LENGTH: 22
<212> TYPE: DNA
<213> ORGANISM: Artificial
<220> FEATURE:
<223> OTHER INFORMATION: Reverse Primer for Bov-tA2 SINE

<400> SEQUENCE: 8
aatggcaaca cgcttcagta tt                                        22

<210> SEQ ID NO 9
<211> LENGTH: 25
<212> TYPE: DNA
<213> ORGANISM: Artificial
<220> FEATURE:
<223> OTHER INFORMATION: Probe for the PRE-1 intra-SINE porcine
      detection assay

<400> SEQUENCE: 9
tttgatccct ggccttgctc agtgg                                     25

<210> SEQ ID NO 10
<211> LENGTH: 20
<212> TYPE: DNA
<213> ORGANISM: Artificial
<220> FEATURE:
<223> OTHER INFORMATION: Forward Primer for porcien PRE-1 SINE

<400> SEQUENCE: 10
ggccttgctc agtgggttaa                                           20

<210> SEQ ID NO 11

```
<211> LENGTH: 20
<212> TYPE: DNA
<213> ORGANISM: Artificial
<220> FEATURE:
<223> OTHER INFORMATION: Reverse Primer for porcine PRE-1 SINE

<400> SEQUENCE: 11
gggatccaag ccacatctgt                                               20

<210> SEQ ID NO 12
<211> LENGTH: 20
<212> TYPE: DNA
<213> ORGANISM: Artificial
<220> FEATURE:
<223> OTHER INFORMATION: Probe for porcine detection assay

<400> SEQUENCE: 12
acagctcacg gcaacgccgg                                               20
```